(12) United States Patent
Sklar (10) Patent No.: US 9,216,125 B2
(45) Date of Patent: Dec. 22, 2015

(54) SURGICAL HEAD HOLDER AND SURGICAL ACCESSORIES FOR USE WITH SAME (76) Inventor: Frederick H. Sklar, Waxahachie, TX (US)

( * ) Notice: Subject to any disclaimer, the term of this patent is extended or adjusted under 35 U.S.C. 154(b) by 178 days.

(21) Appl. No.: 13/556,119

(22) Filed: Jul. 23, 2012

(65) Prior Publication Data

US 2013/0019877 A1   Jan. 24, 2013

Related U.S. Application Data (60) Provisional application No. 61/510,689, filed on Jul. 22, 2011.

(51) Int. Cl.
*A61G 13/12* (2006.01)
*A61B 19/00* (2006.01)

(52) U.S. Cl.
CPC ............. *A61G 13/121* (2013.01); *A61B 19/203* (2013.01)

(58) Field of Classification Search
CPC ......... A61F 13/12; A61F 5/37; A61F 5/3707; A61F 5/05; A61F 5/055; A61G 13/121; A61B 19/201; A61B 19/203; A61B 17/02; A61B 17/0293
USPC ................ 128/845, 846, 857; 602/17, 32, 33; 5/622, 636, 637, 640, 643; 606/130
See application file for complete search history.

(56) References Cited

U.S. PATENT DOCUMENTS

| 3,522,799 A | * | 8/1970 | Gauthier | ...................... | 600/215 |
| 3,810,462 A |   | 5/1974 | Szpur |   |   |
| 4,108,426 A | * | 8/1978 | Lindstroem et al. | ............... | 5/637 |
| 4,143,652 A |   | 3/1979 | Meier et al. |   |   |
| 4,254,763 A |   | 3/1981 | McCready et al. |   |   |
| 4,457,300 A |   | 7/1984 | Budde |   |   |
| 4,700,691 A | * | 10/1987 | Tari et al. | ........................... | 5/622 |
| 5,284,129 A |   | 2/1994 | Agbodoe et al. |   |   |
| 5,529,358 A | * | 6/1996 | Dinkler et al. | ................ | 600/233 |

(Continued)

FOREIGN PATENT DOCUMENTS

| JP | S55-052747 | 4/1980 |
| JP | H09-075369 | 3/1997 |
| JP | H09-147142 | 6/1997 |

OTHER PUBLICATIONS

International Search Report, PCT/US12/47894, Oct. 18, 2012.

*Primary Examiner* — Nicholas Woodall
*Assistant Examiner* — Raymond E Harris
(74) *Attorney, Agent, or Firm* — Scott T. Griggs; Griggs Bergen LLP (57) ABSTRACT

A surgical head holder and accessories for use with the same are disclosed. In one embodiment, a horseshoe shaped head support includes two wings pivotally coupled that adjust the angle therebetween. Arcuate base members are coupled to the wings to accept a plurality of placement subassemblies, which are circumferentially adjustably positioned and secured within the channels. Each placement subassembly is configured to receive a skull pin and provide adjustable horizontal, vertical, and angular positioning of the skull pin with respect to the arcuate base. A table attachment supports the horseshoe shaped head support and is adapted to be selectively and rigidly coupled to an operating table. The table attachment includes a vertical body, a horizontal generally u-shaped bar adjustably intersecting therewith, and an attachment member extending therefrom for coupling to the operating table. Various neurosurgical accessories may be rigidly coupled to the table attachment.

21 Claims, 7 Drawing Sheets

(56) References Cited

U.S. PATENT DOCUMENTS

| | | | |
|---|---|---|---|
| 5,537,704 A * | 7/1996 | Dinkler | 5/622 |
| 6,306,085 B1 | 10/2001 | Farascioni | |
| 6,416,468 B2 | 7/2002 | Deckman et al. | |
| 6,602,190 B2 | 8/2003 | Dobrovolny | |
| 7,117,551 B1 * | 10/2006 | Dinkler et al. | 5/637 |
| 7,232,411 B2 * | 6/2007 | Dinkler et al. | 600/233 |
| 7,326,177 B2 | 2/2008 | Williamson, IV et al. | |
| 7,730,563 B1 * | 6/2010 | Sklar et al. | 5/637 |
| 8,037,884 B2 * | 10/2011 | Weinstein et al. | 128/845 |
| 8,801,711 B2 * | 8/2014 | Solomon et al. | 606/59 |
| 2005/0277832 A1 * | 12/2005 | Foley et al. | 600/426 |
| 2008/0269777 A1 * | 10/2008 | Appenrodt et al. | 606/130 |
| 2011/0168184 A1 | 7/2011 | Sklar | |
| 2014/0378774 A1 * | 12/2014 | Wooster | 600/230 |

\* cited by examiner

SURGICAL HEAD HOLDER AND SURGICAL ACCESSORIES FOR USE WITH SAME

PRIORITY STATEMENT & CROSS-REFERENCE TO RELATED APPLICATIONS

This application claims priority from U.S. Patent Application No. 61/510,689, entitled "Pediatric Headrest and Accessories for Use with Same" and filed on Jul. 22, 2011, in the name of Frederick H. Sklar; which is hereby incorporated by reference for all purposes.

TECHNICAL FIELD OF THE INVENTION

This invention relates, in general, to the field of surgical appliances and, in particular, to a surgical head holder and surgical accessories for use with the same during surgical operations on the brain.

BACKGROUND OF THE INVENTION

At present, systems that connect surgical headrests to the operating table do not specifically allow for rigid connection of various brain retractor systems. Some self-retaining retractor systems are designed to be attached directly to standard three pin headrests with pressure clamps that, when used, gather draping material into the clamp and can therefore become dislodged or loosened. Other retractor systems attach to the operating table itself, but require relatively long horizontal rods to hold the frame in place. These horizontal connecting rods can interfere with the placement of image guidance hardware and can limit how close the retractor apparatus can be to the surgical wound. Other existing systems allow rigid attachment of image guidance connection hardware to traditional three pin headrest devices, but these attachments are relatively large, somewhat awkward to use, and in close proximity to the patient's head.

SUMMARY OF THE INVENTION

It would be advantageous to achieve a surgical head holder that would enable rigid connection of various brain retractor systems and other surgical accessories during operations on the brain. It would also be desirable to enable a mechanical-based solution that would provide for an integrated surgical system allowing for the efficient and simultaneous use of surgical accessories without sacrificing functionality. To better address one or more of these concerns, a surgical head holder, which may be utilized as a pediatric headrest, and accessories for use with the same are disclosed. In one embodiment, a horseshoe shaped head support includes first and second wings pivotally coupled to a body to adjust the angle therebetween. A gel pad is superposed on the horseshoe shaped head support. First and second arcuate base members are coupled to the first and second wings, respectively, to accept a plurality of placement subassemblies, which are circumferentially adjustably positioned and secured within the channels. Each placement subassembly is configured to receive a skull pin and provide adjustable horizontal, vertical, and angular positioning of the skull pin with respect to the arcuate base.

A table attachment supports the horseshoe shaped head support and is adapted to be selectively and rigidly coupled to an operating table. The table attachment includes a vertical body, a horizontal u-shaped bar adjustably intersecting therewith, and an attachment member extending therefrom for coupling to the operating table. Various surgical accessories may be rigidly coupled to the table attachment. Such accessories may include a surgical retractor, image guidance hardware frame, or a light and mirror assembly, for example. These and other aspects of the invention will be apparent from and elucidated with reference to the embodiments described hereinafter.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which.

DETAILED DESCRIPTION OF THE INVENTION

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention, and do not delimit the scope of the present invention.

Figure 1:
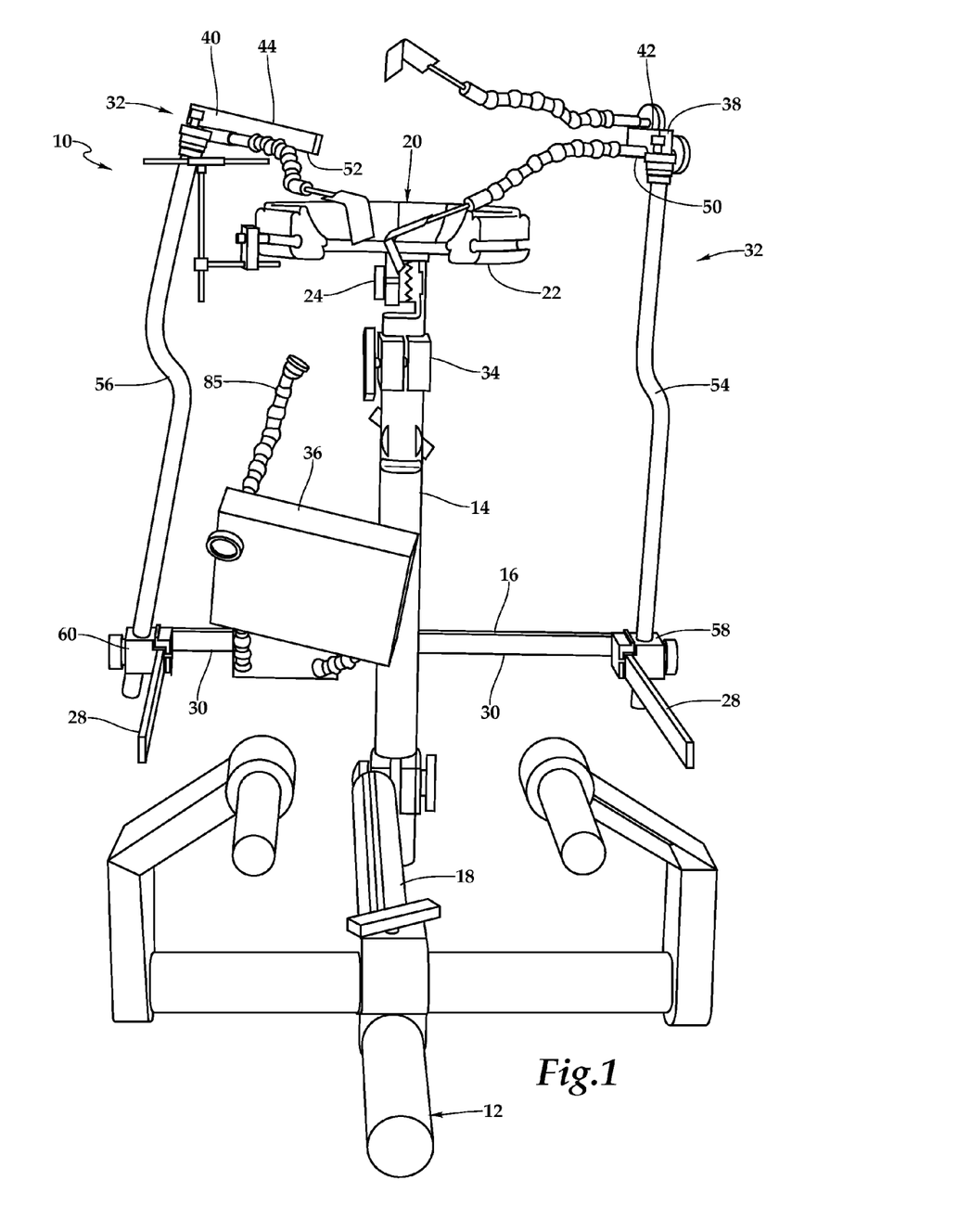
FIG. 1 is a front elevation view of one embodiment of the surgical head holder and surgical accessories for use with the same depicted according to the teachings presented herein.
Figure 2:
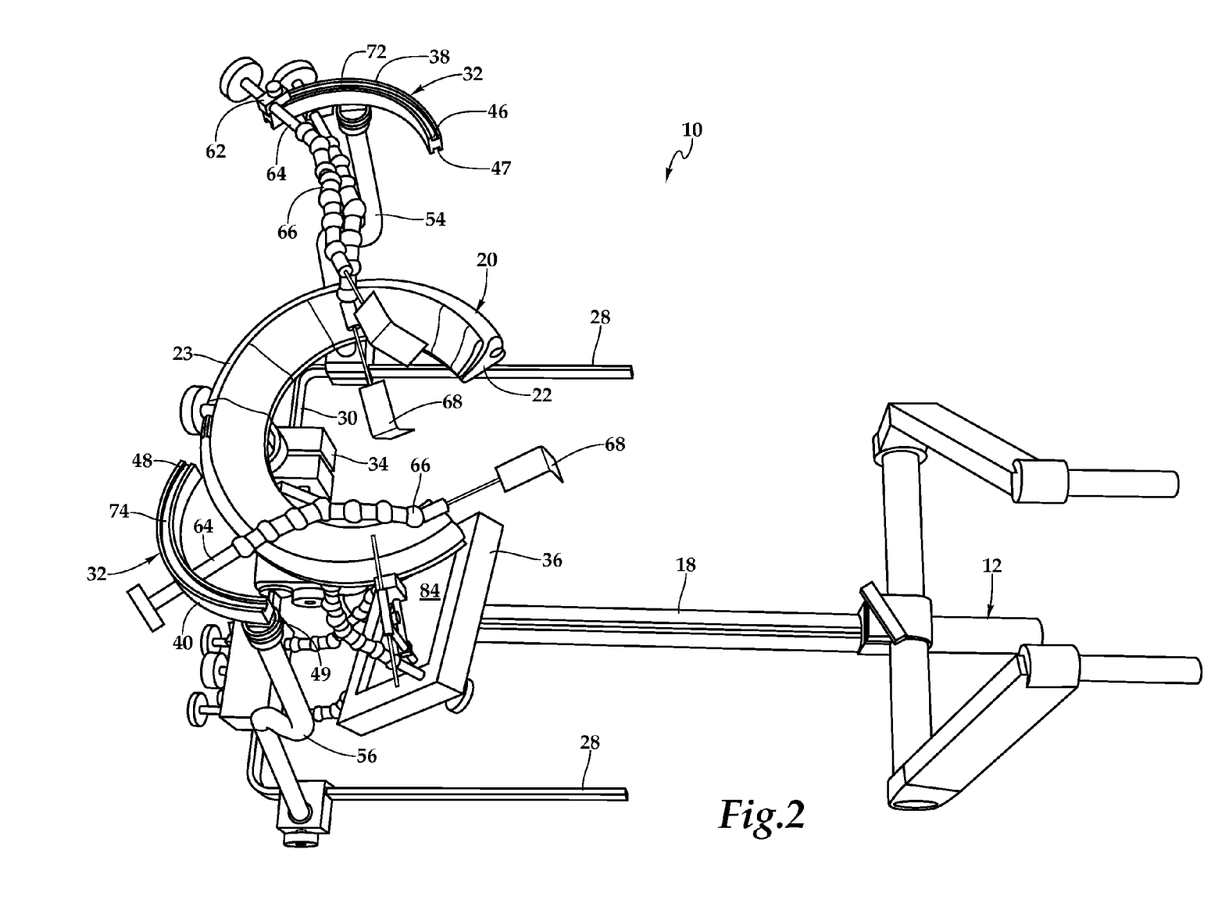
FIG. 2 is top plan view of the surgical head holder and surgical accessories depicted in FIG. 1.
Figure 3:
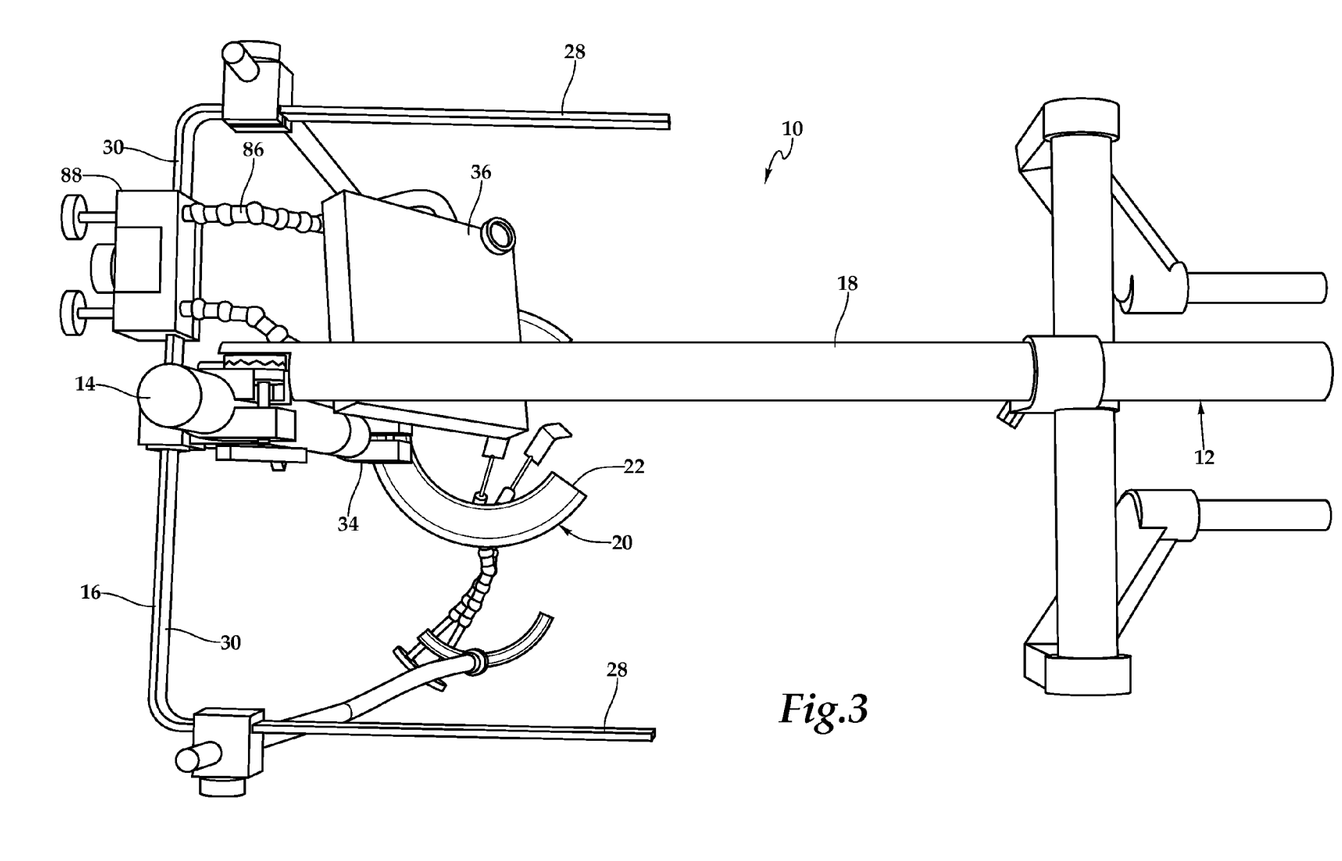
FIG. 3 is a bottom plan view of the surgical head holder and surgical accessories depicted in FIG. 1.
Figure 4:
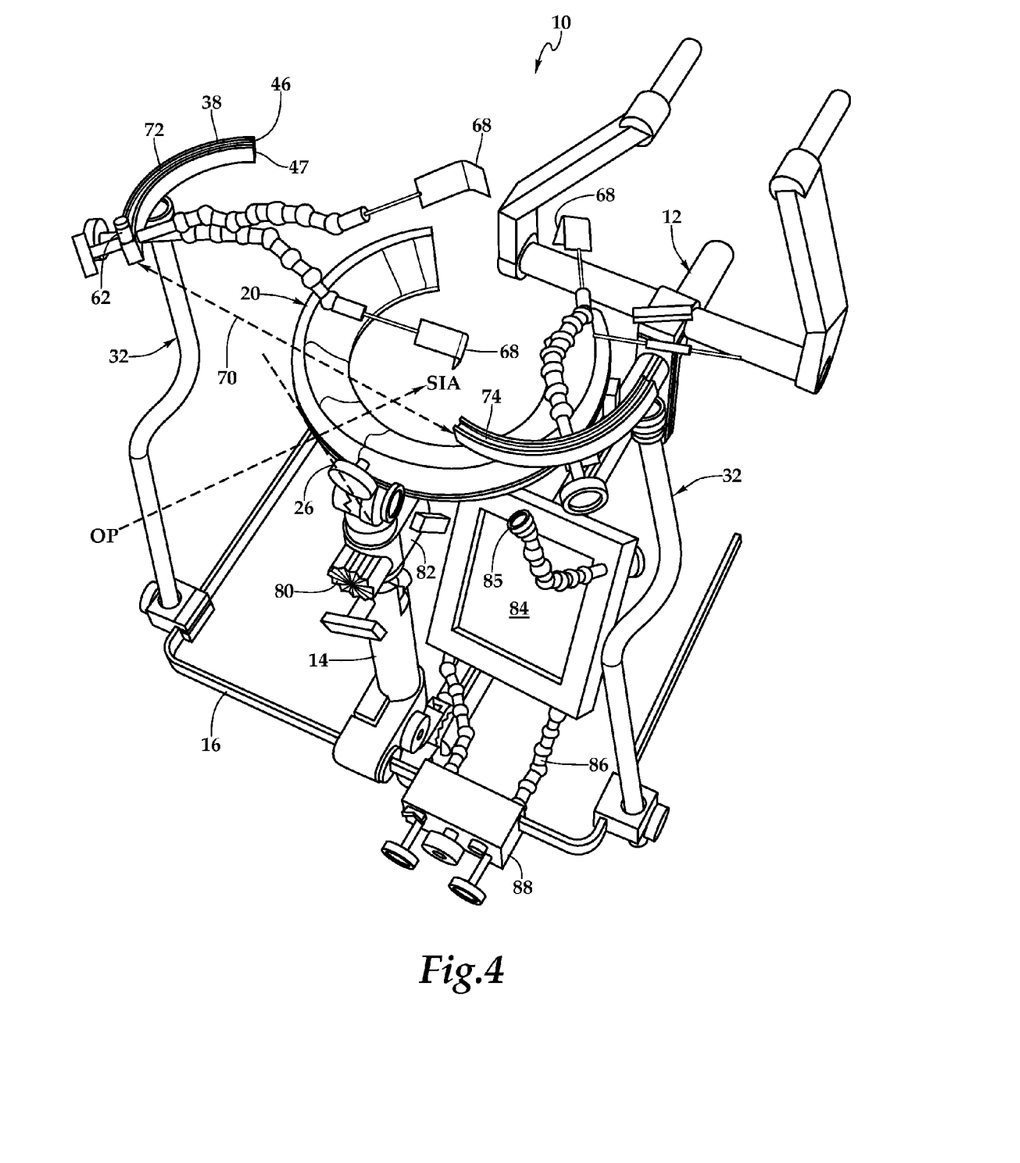
FIG. 4 is a rear elevation view of the surgical head holder and surgical accessories depicted in FIG. 1.

Referring initially to FIGS. 1 through 4, therein is depicted one embodiment of a surgical head holder for skull stabilization during neurosurgical and orthopedic procedures, which is schematically illustrated and designated 10. A table attachment 12 is adapted to be selectively and rigidly coupled to an operating table. The table attachment 12 includes an adjustable vertical body 14, a horizontal generally u-shaped bar 16 adjustably intersecting therewith, and an attachment member 18 extending therefrom for coupling to the operating table in a standard or universal manner.

A head support or surgical headrest 20 is adapted to be positioned subjacent to and to provide support to the weight of the skull. The head support 20 is configured to accept the skull in a position selected from the group consisting of prone, supine, lateral and combinations thereof. A base member 22 is coupled to the head support 20 and at least partially circumscribes a perimeter thereof. As shown, the base member 22 is adjustably coupled to the table attachment 12 by a coupling member 24, which in one embodiment provides multiple degrees of freedom, including vertical, horizontal, and angular.

An unobstructed operating window 26 provides access from an operating position (OP) to the surgical incision area (SIA), as represented by the area circumscribed by the base member 22. At least one surgical accessory is coupled to the generally u-shaped bar 16, which defines a plane having a first axis 28 and a second axis 30 of attachment. The first axis 28 of attachment runs parallel to the attachment member and operating table to laterally offset surgical accessories from the unobstructed operating window 26 and remove unnecessary portions of the surgical accessories from the operating window 26. The second axis 30 of attachment provides coupling for surgical accessories which are required to be within the surgeon's general line-of-sight, but outside or below the operating window 26.

Non-limiting examples of the surgical accessories include a surgical retractor 32, image guidance hardware frame 34, and a light and mirror assembly 36, for example. The surgical retractor 32 retains tissue, membrane, organs and the like in retracted position in an incision during a surgical procedure. Two ring members 38, 40 are included and each has an unobstructed planar upper surface 42, 44 and a continuous, circumferentially outwardly opening channel 46, 48 around its periphery. Each of the two ring members 38, 40 further comprise unobstructed planar lower surfaces 50, 52. Respective support apparatuses 54, 56 connected to each of the two ring members 38, 40 in order to hold each of the respective ring members 38, 40 in a position over the surgical incision and lateral and outside of the operating window 26. Each of the respective support apparatuses 54, 56 is mounted to the respective ring 38, 40 below the respective outwardly opening channel 46, 48 and projecting outwardly from the periphery thereof. Each of the respective support apparatuses 54, 56 is rigidly and adjustably secured to the horizontal u-shaped bar by connectors 58, 60.

A retractor arm holder 62 having a projection 64 is slidably captured within one of the outwardly opening channels 46, 47, 48, 49. The retractor arm holder 62 extends outwardly from one of the ring members 38, 40 such that the projection is movable within the outwardly opening channel around the periphery of the ring member to position the arm holder 62 at a desired location therealong. A retractor arm 66 includes a blade 68 attached thereto and the retractor arm 66 is mounted to the arm holder 62 outwardly of the ring so that the retractor arm 66 is configured to pass below and inwardly of the associated ring member. As shown, in this embodiment, the retractor arm holder 62 is movable around the outwardly opening channel past one of the respective support apparatuses 54, 56 without interference therefrom in order to position the blade 68 relative to the incision. In this manner, the surgical retractor 32 presents a discontinuous, unobstructed upper surface which provides a window span 70, and complements the operating window 26, for unobstructed access to the surgical incision. Additionally, guide rests 72, 74 for stabilizing a surgeon's hand is provided during the operating procedure.

The surgical retractor 32 may involve two or three stainless steel arcs, each entirely independent of the other. As described above and shown in FIGS. 1 through 4, two stainless steel arcs are utilized. As described above, this system allows the surgeon to position each arc to be maximally effective for retraction purposes, to be comfortable as a handrest, and not to restrict access to the surgical wound. Each arc can be brought as close to the patient as is required for effective retraction and hand positioning with much less difficulty than with a closed ring. Moreover, the plane of each arc does not have to be horizontal, nor does it have to be in the same plane orientation as that of the other arc(s). One embodiment is an 8 inch segmental arc circumference with a four (4) inch radius. The system includes multiple sets of three identically sized arcs. Each set has a different arc radius and/or segment length.

With this configuration, the surgical head holder disclosed herein provides for rigid connection of the surgical retractor 32 to the operating table without the surgical retractor being coupled to the headrest or other awkward coupling. The tubular based system presented herein provides versatility of positional adjustment of the surgical head holder in all planes of clinical pertinence, an adjustable U-shaped bar 16 that is positioned on a vertical (or semi-vertical) member 14 of the tubular table attachment 12 that may support the self-retaining retractor system, surgeon hand supports, and the light and mirror assembly 36 that allows for intra-operative visualization of the patient's eyes when the patient is in the prone position.

As illustrated, each arc or ring member 38, 40 has channels 46, 47, 48, 49 or slots along both the top and bottom that can accommodate brain retractor arms. A low-profile attachment design provides secure fixation of the adjustable brain retractors to the arcs or channels 46, 47, 48, 49. The retractor arm 66 can be secured to either the top or bottom slots 46, 47, 48, 49 and this feature eliminates the extra ninety (90) degree turn of the retractor arm in prior art systems, such as the Budde Halo system, in which the retractor arm attaches to the slotted outside of the ring. This repositioning of the adjustable brain retractor attachments represents a significant improvement over the Budde Halo system and provides greater stability and safety in retraction. In addition, the bottom slots 47, 49 also accommodates a support apparatus 54, 56 that is secured to the U-shaped bar 16 below. Thus, each arc segment is rigidly supported by a connecting rod to the U-shaped bar, and this connecting linkage can be positioned anywhere along the arc or ring member for maximum versatility of positioning and efficiency of usage.

The light and mirror assembly 36 includes a mirror 84 and a light 85 that is adjustably secured thereto. With respect to the light and mirror, positioning of a prone child's head, by way of example, in a horseshoe headrest requires particular attention to fitting the headrest to the child's facial anatomy so that there is no pressure on the eyes. If a child's head were to move slightly in a traditional horseshoe headrest during the course of an operation, a gel pad or its metal support may exert unsafe pressure on an eye. This can result in permanent injury or even blindness.

Accordingly, a pediatric neuroanesthesiologist may wish to check and recheck the position of a child's eyes relative to the headrest and gel pads. Some occasionally use a mirror and flashlight for this purpose, although maneuvering under wet surgical drapes during a neurosurgical procedure can be problematic. As such, the present embodiment includes a light and mirror assembly 36 that attaches to the U-shaped bar 18 by multi-linked arms 86 and a rigid connection clamp 88. A battery operated LED light is attached to the mirror frame with an adjustable arm. Both mirror and light can be positioned for good visualization of the patient's eyes prior to draping. A switch for the light can be incorporated into a U-bar clamp 88, which couples the light and mirror assembly 36. A red light adjacent to the light switch can provide indication when the battery needs to be replaced. The battery can be incorporated into the U-bar clamp 88 as well. With this system, the anesthesiologist can check the patient's positioning in the horseshoe headrest at any time without difficulty.

With respect to the attachment of image guidance hardware 34, it is customary to attach the patient frame for image guidance directly to traditional three pin headrests with a standard starburst attachment device. How close the image guidance frame is to the surgical wound can influence image guidance accuracy, and the frame must be positioned reasonably close to the surgical site. On the other hand, image guidance accuracy does not directly depend on the linkage system connecting the patient image guidance frame directly to the surgical headrest. The connections must be rigid, however, because there can be no movement within the connections or any alteration in the geometric relationships. In other words, the image guidance frame can have a rigid relationship to the patient's headrest by being fixed to rigid table attachment 12, preferably close to the surgical headrest 20. In the present embodiment, a starburst attachment site 80 is configured to mate with a counterpart starburst attachment 82 secured to the adjustable vertical body 14 proximate the base member 22.

Figure 5:
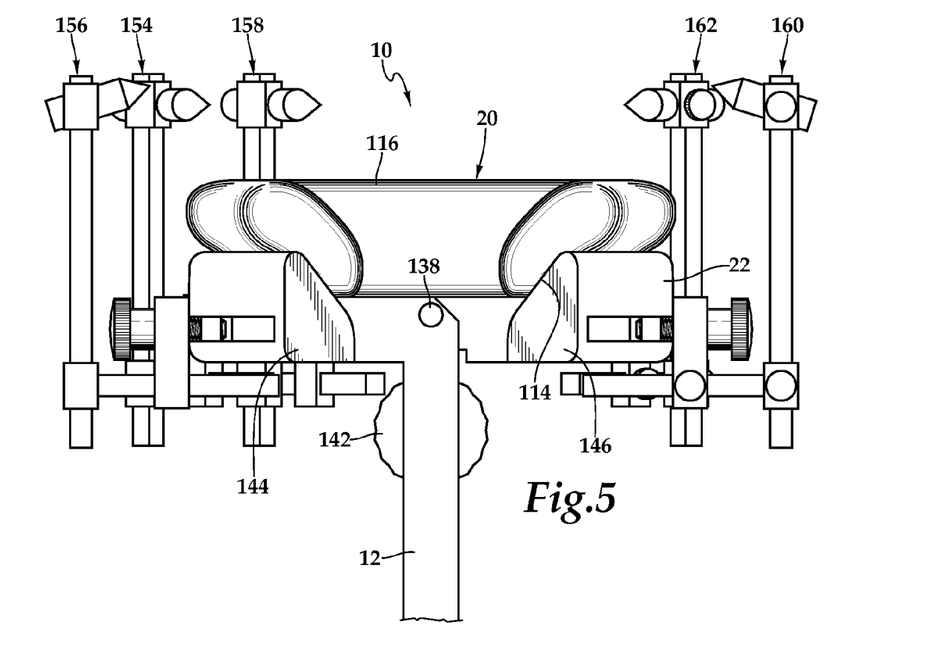
FIG. 5 is a front elevation view of one embodiment of the surgical headrest for skull stabilization during neurosurgical, including pediatric neurosurgical, and orthopedic procedures.
Figure 6:
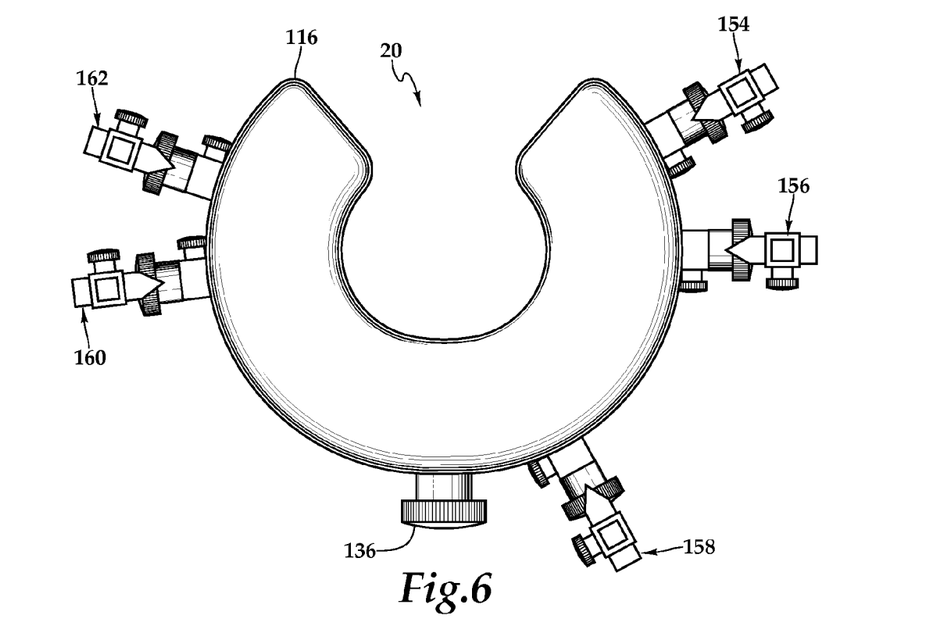
FIG. 6 is top plan view of the surgical headrest of FIG. 5.
Figure 7:
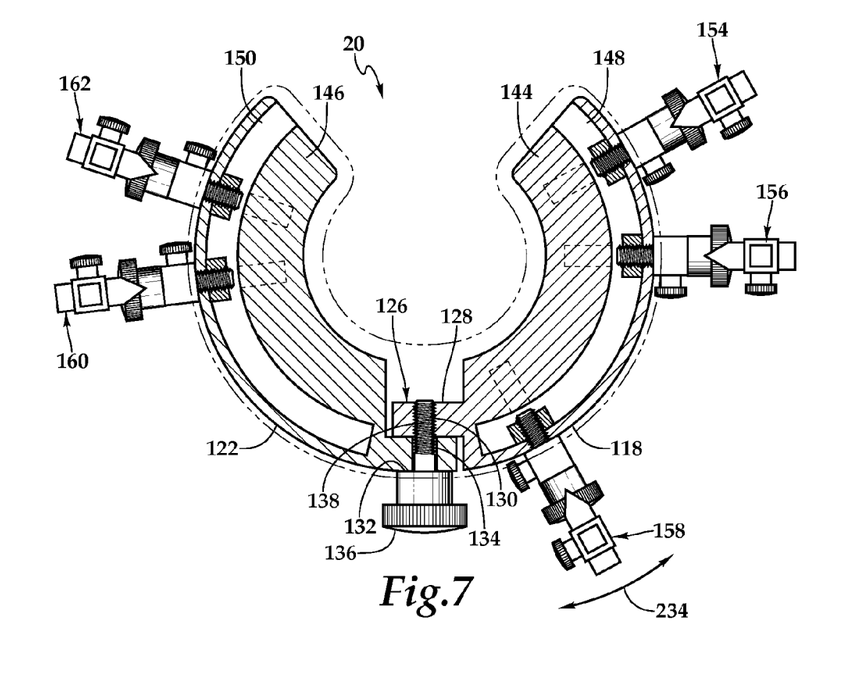
FIG. 7 is a top cross-sectional view of the surgical headrest of FIG. 5.
Figure 8:
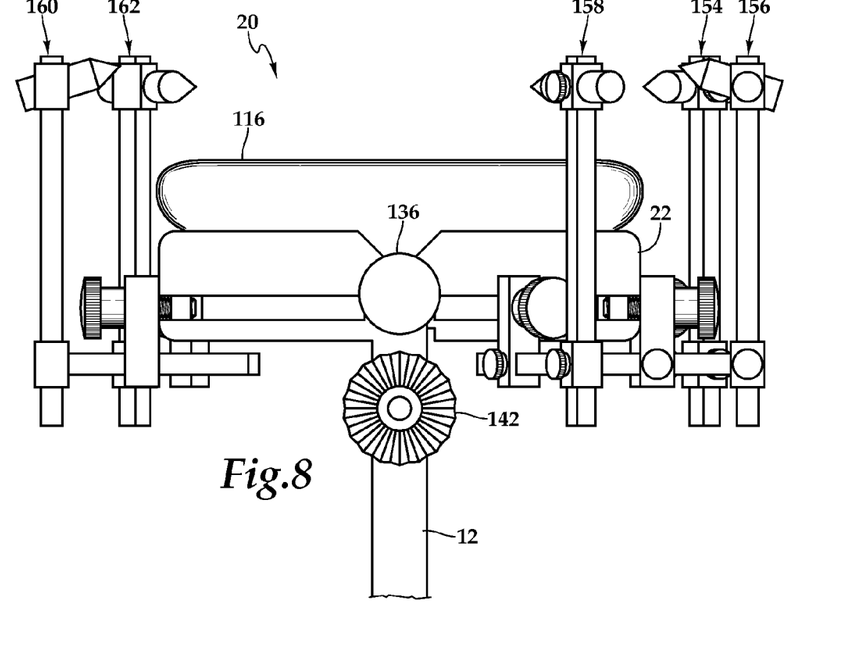
FIG. 8 is a rear elevation view of the surgical headrest of FIG. 5.
Figure 9:
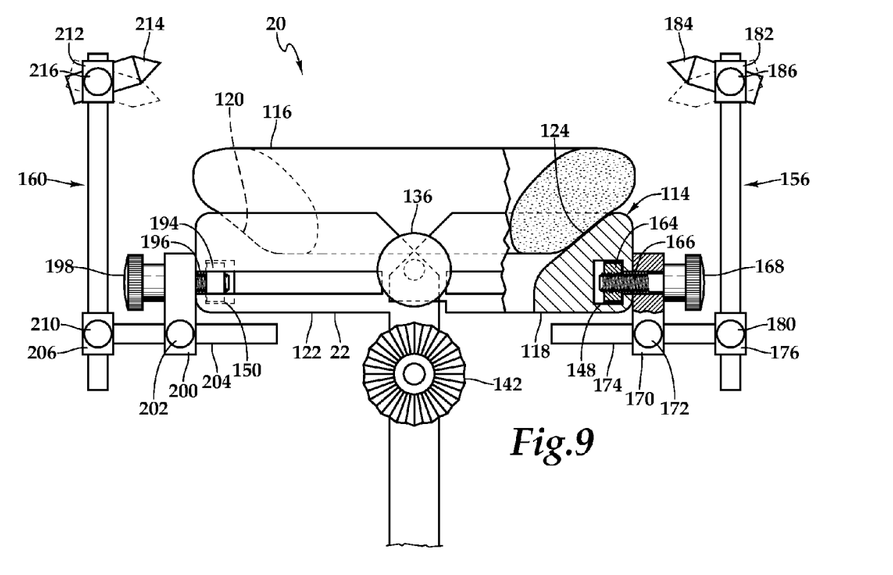
FIG. 9 is a rear cross-sectional view of the surgical headrest of FIG. 5.
Figure 10:
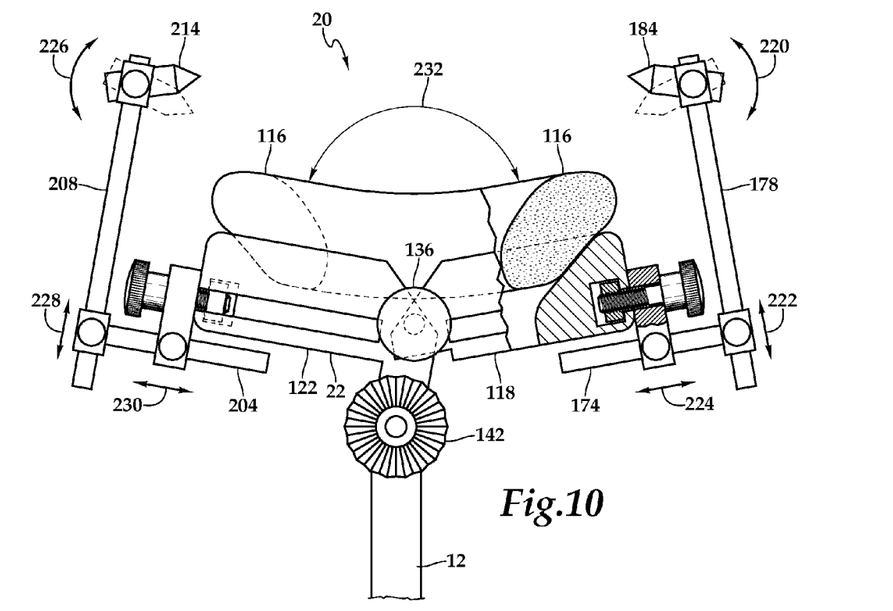
FIG. 10 is a rear cross-sectional view of the surgical headrest of FIG. 5, wherein the position of the surgical headrest is being adjusted when compared to FIG. 9.

Referring now to FIGS. 5 through 10, therein is depicted one embodiment of the surgical head holder 10 and particularly the head support 20 in further detail. In one embodiment, the base member 22 includes a horseshoe shaped head support 114, which may take the form of a horseshoe shaped gel padded head holder, is adapted to be positioned subjacent to and provide support to the weight of the head or skull with padding in order to prevent deformation. As depicted, an ergonomic gel pad 116 covers the horseshoe shaped head support 114 in order to accept the head or skull and provide discrete pressure. Stainless steel, aluminum, or carbon fiber can be used to make the horseshoe and body components, each furnishing distinct clinical advantages and the selection of which depending on the planned application. Stainless steel provides the most durability. Aluminum reduces the weight of the surgical head holder. Carbon fiber allows the use of the surgical head holder with intraoperative MRI scanning.

In one embodiment, the base member 22 includes two halves each having an ergonomic curved surface. As shown, wing 118 includes ergonomic curved surface 120 and wing 122 includes ergonomic curved surface 124. A pivot joint 126 is at the interface of the wings 118, 122. Overlapping extension 128 of wing 118 having threaded bore 134 aligns with overlapping extension 132 of wing 122 having threaded bore 130 such that locking knob 136 can selectively loosen and tighten. The locking knob 136 includes threaded fastener 138 extending therefrom for mating with the aligned threaded bores 130, 134.

Upon loosening the locking knob 136 and the threaded fastener 138, the wings 118, 122 are movable to provide a continuous variety of angles therebetween in order to provide a wide range of adjustability to accommodate different sizes of heads and different positions, whether prone, supine, lateral or combinations thereof. When the desired angle 232 between the wings 118, 122 is reached, the locking knob 136 is tightened and the width of the base member 22 is thereby set (compare FIGS. 9 and 10). In this way, the surgical head holder 10 can be adjusted to be used with tiny infants, a distinct advantage over traditional headrests now available. The surgical headholder 10 may be attached to operating table clamps that are commercially available and in use with other headrests. As shown, however, and knurled female receptacle knob 142 secure the head support 20 to the adjustable vertical body 14 and operating table in a variety of positions.

The base member 22 has an arcuate base member 144 and an arcuate base member 146 is coupled to the body such that the arcuate base members 144, 146 at least partially circumscribe a perimeter of the base member 22. Respective connection members, which may have the form of channels, slots, recessed slots, or engagement mounting points for example, are located within the arcuate base members 144, 146. As shown channels 148, 150 are depicted. Multiple placement subassemblies 154, 156, 158, 160, 162 are circumferentially adjustably positioned and secured to the channels 148, 150. Enabled by a series of adjustable clamps and bars, each placement subassembly 154-162 is configured to receive a pin and provide adjustable horizontal, vertical, and angular positioning of the pin with respect to the channels 148, 150. Each of the placement subassemblies, which include a skull pin, is adapted to provide lateral discrete pressure to the skull in order to stabilize the skull. In one implementation, each of the pins comprise skull immobilizing pin subassemblies. In this implementation, stainless steel skull pins are suitable for use with the pin subassemblies. Processing of all components may be by manual or CNC milling and/or lathe operations. In particular, the skull pins selected are non-weight supporting and are adapted to provide adjustable horizontal, vertical, and angular positioning of the skull pin with respect to the arcuate base. With this arrangement, the head support is configured to support the weight of the skull and the skull pins configured to provide lateral discrete pressure, thereby stabilizing the skull and separating the dual functions of support and fixation.

With respect to placement subassembly 154, as shown, the placement subassembly 154 has a locking bar 164 in the form of a dovetail that slides in the channel 148 and a locking screw 166 via locking knob 168 engages the locking bar 164 by being threaded therein and bearing against the locking bar 164 and channel 148. As the locking screw 66 is tightened, a tight compression fit is developed within the channel 148. The placement subassembly 154 may be moved circumferentially around in the channel 148 to a desired location, and the placement subassembly can be adjusted vertically and horizontally. As shown a pin post carrier 170 selectively tightened by a locking knob 172 supports a horizontal pin post 174 and permits the horizontal pin post to slide to and from the channel 148. With respect to vertical movement, a pin post carrier 176 supports a vertical pin post with knob 180 providing for selective tightening. A skull pin carrier 182 supports skull pin 184, the angle of which may be selectively adjusted by knob 186.

By way of example, placement subassembly 160 includes a locking bar 194, screw 196, and locking knob 198 for circumferential placement of the skull pin 214. A pin post carrier 200, locking knob 202, and horizontal pin post 204 provide horizontal placement of the skull pin 214. A pin post carrier 206, a vertical pin post 208, and a knob 210 furnish vertical placement of the skull pin 214. A skull pin carrier 212 and knob 216 control the angle of skull pin 214. To illustrate this movement, arrow 220 depicts the pivoting of the skull pin 184, arrow 222 depicts the vertical movement of retraction pin post 178, and arrow 224 depicts the horizontal placement of the skull pin 184. Likewise, arrows, 226, 228, 230 depict similar ranges of movement for the skull pin 214.

The surgical head holder presented herein allows neurosurgical and orthopedic operations on infants and children of all ages as a pediatric headrest, as well as adults. It will be appreciated that the scale of the surgical head holder will vary will application. Prior to the development of the concept of the surgical head holder, traditional headrests use three pins to support the weight of the patient's head and to prevent any movement. Unlike traditional headrests, the surgical head holder, in one implementation, separates the dual functions into two components: (1) the surgical head holder supports the weight of the head with a padded horseshoe-shaped device; and 2) the surgical head holder provides rigid fixation of the skull with multiple, adjustable, low torque pins that can be moved about the arc of the headrest. Although this system can be attached to an operating table with a variety of existing table attachment hardware, a tubular attachment system described herein allows for the efficient usage of accessories to the surgical head holder. In one embodiment, these accessories include the following: (1) self-retaining brain retractors and surgeon hand supports; (2) attachment for image guidance; and (3) attachment of a light and mirror assembly for intra-operative visualization of the patient's eyes. An integrated system allows for the efficient and simultaneous use of these surgical accessories without interfering with the functions of one or the others.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A surgical head holder for skull stabilization during neurosurgical and orthopedic procedures, the surgical head holder comprising:
    a table attachment adapted to be selectively and rigidly coupled to an operating table, the table attachment including an adjustable vertical body, a horizontal continuous, u-shaped bar adjustably intersecting therewith, and an attachment member extending therefrom for coupling to the operating table;
    the horizontal continuous, u-shaped bar defining a horizontal plane having two first axes and a second axis of surgical accessory attachment, the two first axes of surgical accessory attachment being perpendicular to the second axis of surgical accessory attachment;
    an unobstructed operating window providing access from an operating position to a surgical incision;
    the two first axes of surgical accessory attachment runs parallel to the attachment member and operating table to laterally offset a first surgical accessory from the unobstructed operating window and remove unnecessary portions of the first surgical accessory from the unobstructed operating window;
    the second axis of surgical accessory attachment runs perpendicular to the attachment member and operating table to provide coupling for a second surgical accessory which is required to be within a surgeon's general line-of-sight, and outside and below the unobstructed operating window;
    a head support adapted to be positioned subjacent to and to provide support to a weight of a skull, the head support configured to accept the skull in a position selected from the group consisting of prone, supine, lateral and combinations thereof;
    a base member coupled to the head support and at least partially circumscribing a perimeter thereof, the base member having respective channels, the base member being adjustably coupled to the table attachment;
    a plurality of placement subassemblies circumferentially adjustably positioned and secured to the respective channels of the base member, each placement subassembly configured to receive a skull pin and provide adjustable horizontal, vertical, and angular positioning of the skull pin with respect to the arcuate base;
    each of the skull pins adapted to provide lateral discrete pressure to the skull in order to stabilize the skull, each of the skull pins being non-weight supporting;
    the head support configured to support the weight of the skull and the skull pins configured to provide lateral discrete pressure, thereby stabilizing the skull and separating the dual functions of support and fixation; and
    the first and second surgical accessory accessories coupled to the horizontal continuous, u-shaped bar, the first surgical accessory coupled to one of the first axes and the second surgical accessory coupled to the second axis.

2. The surgical head holder as recited in claim 1, further comprising a surgical retractor for retaining tissue, membrane, organs and the like in retracted position in the surgical incision during a surgical procedure, the surgical retractor comprising:
    two ring members, each ring member includes an unobstructed planar upper surface and a continuous, circumferentially outwardly opening channel around its periphery;
    respective support apparatuses connected to each of the two ring members, each of the support apparatuses configured to hold the respective ring member in a position over the surgical incision, each of the respective support apparatuses mounted to the ring below the outwardly opening channel and projecting outwardly from the periphery thereof;
    the respective support apparatuses being rigidly secured to the horizontal continuous, u-shaped bar;
    a retractor arm holder having a projection slidably captured within one of the outwardly opening channels, the retractor arm holder extending outwardly from one of the ring members, the projection being movable within the outwardly opening channel around the periphery of the ring to position the arm holder at a desired location therealong;
    a retractor arm having a blade attached thereto, the retractor arm being mounted to the arm holder outwardly of the ring so that the retractor arm is configured to pass below and inwardly of the associated ring member;
    the retractor arm holder being movable around the outwardly opening channel past one of the respective support apparatuses without interference therefrom, to position the blade relative to the surgical incision; and
    the surgical retractor presenting a discontinuous, unobstructed upper surface which provides a window for unobstructed access to the surgical incision, and a guide rest for stabilizing the surgeon's hand during the surgical procedure.

3. The surgical head holder as recited in claim 2, wherein the two ring members each comprise the unobstructed planar upper surface, an unobstructed planar lower surface and respective continuous, circumferentially outwardly opening channels around each periphery.

4. The surgical head holder as recited in claim 1, further comprising an image guidance hardware frame, the image guidance hardware frame comprising:
    a starburst attachment site configured to mate with a counterpart starburst attachment secured to the vertical body proximate the base member.

5. The surgical head holder as recited in claim 1, further comprising a mirror adjustably secured to the vertical body by a retracting arm.

6. The surgical head holder as recited in claim 1, further comprising a mirror adjustably secured to the horizontal continuous, u-shaped bar by a retracting arm.

7. The surgical head holder as recited in claim 1, further comprising a second neurosurgical accessory rigidly coupled to the table attachment.

8. A surgical head holder for skull stabilization during neurosurgical and orthopedic procedures, the surgical head holder comprising:
  a table attachment adapted to be selectively and rigidly coupled to an operating table, the table attachment including an adjustable vertical body, a horizontal continuously, u-shaped bar adjustably intersecting therewith, and an attachment member extending therefrom for coupling to the operating table; the horizontal continuously, u-shaped bar defining a horizontal plane having two first axes and a second axis of surgical accessory attachment;
  an unobstructed operating window providing access from an operating position to a surgical incision;
  the two first axes of surgical accessory attachment being perpendicular to the second axis of surgical accessory attachment; the two first axis of surgical accessory attachment runs parallel to the attachment member and operating table to laterally offset a first surgical accessory from the unobstructed operating window and remove unnecessary portions of the first surgical accessory from the unobstructed operating window;
  the second axis of surgical accessory attachment runs perpendicular to the attachment member and operating table to provide coupling for a second surgical accessory which is required to be within a surgeon's general line-of-sight, and outside and below the unobstructed operating window;
  a head support adapted to be positioned subjacent to and to provide support to a weight of a skull, the head support configured to accept the skull in a position selected from the group consisting of prone, supine, lateral and combinations thereof;
  a base member coupled to the head support and at least partially circumscribing a perimeter thereof, the base member having respective channels, the base member being adjustably coupled to the table attachment;
  a plurality of placement subassemblies circumferentially adjustably positioned and secured to the respective channels of the base member, each placement subassembly configured to receive a skull pin and provide adjustable horizontal, vertical, and angular positioning of the skull pin with respect to the arcuate base;
  each of the skull pins adapted to provide lateral discrete pressure to the skull in order to stabilize the skull, each of the skull pins being non-weight supporting;
  the head support configured to support the weight of the skull and the skull pins configured to provide lateral discrete pressure, thereby stabilizing the skull and separating the dual functions of support and fixation;
  two ring members, each ring member including an unobstructed planar upper surface and a continuous, circumferentially outwardly opening channel around its periphery;
  respective support apparatuses connected to each of the two ring members, each of the support apparatuses configured to hold the respective ring member in a position over the surgical incision, each of the respective support apparatuses mounted to the ring below the outwardly opening channel and projecting outwardly from the periphery thereof;
  each of the two ring members providing a guide rest surface; and
  the respective support apparatuses being rigidly secured to the horizontal continuously, u-shaped bar.

9. The surgical head holder as recited in claim 8, further comprising a surgical retractor for retaining tissue, membrane, organs and the like in retracted position in the surgery incision during a surgical procedure, the surgical retractor comprising:
  a retractor arm holder having a projection slidably captured within one of the outwardly opening channels, the retractor arm holder extending outwardly from one of the ring members, the projection being movable within the outwardly opening channel around the periphery of the ring to position the arm holder at a desired location therealong;
  a retractor arm having a blade attached thereto, the retractor arm being mounted to the arm holder outwardly of the ring so that the retractor arm is configured to pass below and inwardly of the associated ring member;
  the retractor arm holder being movable around the outwardly opening channel past one of the respective support apparatuses without interference therefrom, to position the blade relative to the surgery incision; and
  the surgical retractor presenting a discontinuous, unobstructed upper surface which provides a window for unobstructed access to the surgical incision, and a guide rest for stabilizing the surgeon's hand during the surgical procedure.

10. The surgical head holder as recited in claim 9, wherein the two ring members each comprise the unobstructed planar upper surface, an unobstructed planar lower surface and respective continuous, circumferentially outwardly opening channels around each periphery.

11. The surgical head holder as recited in claim 8, further comprising an image guidance hardware frame, the image guidance hardware frame comprising:
  a starburst attachment site configured to mate with a counterpart starburst attachment secured to the vertical body proximate the base member.

12. The surgical head holder as recited in claim 8, further comprising a mirror adjustably secured to the vertical body by a retracting arm.

13. The surgical head holder as recited in claim 8, further comprising a mirror adjustably secured to the horizontal continuously, u-shaped bar by a retracting arm.

14. The surgical head holder as recited in claim 8, further comprising a second neurosurgical accessory rigidly coupled to the table attachment.

15. A surgical head holder for skull stabilization during neurosurgical and orthopedic procedures, the surgical head holder comprising:
  a table attachment adapted to be selectively and rigidly coupled to an operating table, the table attachment including an adjustable vertical body, a horizontal continuous, u-shaped bar adjustably intersecting therewith, and an attachment member extending therefrom for coupling to the operating table;
  the horizontal continuous, u-shaped bar defining a horizontal plane having two first axes and a second axis of surgical accessory attachment; the two first axes of surgical accessory attachment being perpendicular to the second axis of surgical accessory attachment;
  an unobstructed operating window providing access from an operating position to a surgical incision;
  the two first axes of surgical accessory attachment runs parallel to the attachment member and operating table to laterally offset a first surgical accessory from the unobstructed operating window and remove unnecessary portions of the first surgical accessory from the unobstructed operating window;

the second axis of surgical accessory attachment runs perpendicular to the attachment member and operating table to provide coupling for a second surgical accessory which is required to be within a surgeon's general line-of-sight, and outside and below the unobstructed operating window;

a head support adapted to be positioned subjacent to and to provide support to a weight of a skull, the head support configured to accept the skull in a position selected from the group consisting of prone, supine, lateral and combinations thereof;

a base member coupled to the head support and at least partially circumscribing a perimeter thereof, the base member being arcuate in shape and including a corresponding outwardly directed arcuate slot, the base member being adjustably coupled to the table attachment;

a plurality of placement subassemblies circumferentially adjustably positioned and secured to the respective arcuate slot of the base member, each placement subassembly configured to receive a skull pin and provide adjustable horizontal, vertical, and angular positioning of the skull pin with respect to the arcuate base;

each of the skull pins being supported by a placement subassembly via a lockable connector; each of the skull pins adapted to provide lateral discrete pressure to the skull in order to stabilize the skull, each of the skull pins being non-weight supporting;

the head support configured to support the weight of the skull and the skull pins configured to provide lateral discrete pressure, thereby stabilizing the skull and separating the dual functions of support and fixation; and at least one surgical accessory coupled to the horizontal continuous, u-shaped bar.

16. The surgical head holder as recited in claim 15, further comprising a surgical retractor for retaining tissue, membrane, organs and the like in retracted position in the surgical incision during a surgical procedure, the surgical retractor comprising:

two ring members, each ring member includes an unobstructed planar upper surface and a continuous, circumferentially outwardly opening channel around its periphery;

respective support apparatuses connected to each of the two ring members, each of the support apparatuses configured to hold the respective ring member in a position over the surgical incision, each of the respective support apparatuses mounted to the ring below the outwardly opening channel and projecting outwardly from the periphery thereof;

the respective support apparatuses being rigidly secured to the horizontal continuous, u-shaped bar;

a retractor arm holder having a projection slidably captured within one of the outwardly opening channels, the retractor arm holder extending outwardly from one of the ring members, the projection being movable within the outwardly opening channel around the periphery of the ring to position the arm holder at a desired location therealong;

a retractor arm having a blade attached thereto, the retractor arm being mounted to the arm holder outwardly of the ring so that the retractor arm is configured to pass below and inwardly of the associated ring member;

the retractor arm holder being movable around the outwardly opening channel past one of the respective support apparatuses without interference therefrom, to position the blade relative to the surgical incision; and the surgical retractor presenting a discontinuous, unobstructed upper surface which provides a window for unobstructed access to the surgical incision, and a guide rest for stabilizing the surgeon's hand during the surgical procedure.

17. The surgical head holder as recited in claim 16, wherein the two ring members each comprise the unobstructed planar upper surface, an unobstructed planar lower surface and respective continuous, circumferentially outwardly opening channels around each periphery.

18. The surgical head holder as recited in claim 15, further comprising an image guidance hardware frame, the image guidance hardware frame comprising:

a starburst attachment site configured to mate with a counterpart starburst attachment secured to the vertical body proximate the base member.

19. The surgical head holder as recited in claim 15, further comprising a mirror adjustably secured to the vertical body by a retracting arm.

20. The surgical head holder as recited in claim 15, further comprising a mirror adjustably secured to the horizontal continuous, u-shaped bar by a retracting arm.

21. The surgical head holder as recited in claim 15, further comprising a second neurosurgical accessory rigidly coupled to the table attachment.

* * * * *